United States Patent [19]

Honore et al.

[11] Patent Number: 5,026,704
[45] Date of Patent: * Jun. 25, 1991

[54] BENZO[F]QUINOXALINE-2,3(1H,4H)-DIONES

[75] Inventors: Tage Honore, Copenhagen; Poul Jacobsen, Rodovre; Flemming E. Nielsen, Virum; Lars Naerum, Gentofte, all of Denmark

[73] Assignee: Novo Nordisk A/S, Bagsvaerd, Denmark

[*] Notice: The portion of the term of this patent subsequent to Dec. 26, 2006 has been disclaimed.

[21] Appl. No.: 456,325

[22] Filed: Dec. 26, 1989

Related U.S. Application Data

[63] Continuation of Ser. No. 268,939, Nov. 8, 1988, Pat. No. 4,948,794.

[30] Foreign Application Priority Data

Nov. 10, 1987 [DK] Denmark .............................. 5862/87
Mar. 16, 1988 [DK] Denmark .............................. 1422/88

[51] Int. Cl.$^5$ ................. A61K 31/495; C07D 241/38; C07D 241/44
[52] U.S. Cl. .................................. 514/250; 514/249; 544/344; 544/354
[58] Field of Search .................... 544/344; 514/250

[56] References Cited

U.S. PATENT DOCUMENTS

| | | | |
|---|---|---|---|
| 3,431,111 | 3/1969 | Brooker et al. | 544/345 |
| 4,889,855 | 12/1989 | Jacobsen et al. | 544/344 |
| 4,912,108 | 3/1990 | Jacobsen et al. | 514/250 |
| 4,948,794 | 8/1990 | Honore et al. | 514/250 |

FOREIGN PATENT DOCUMENTS 283959 9/1988 European Pat. Off. .

OTHER PUBLICATIONS

Jacobsen et al., Chemical Abstracts, vol. 110, No. 75568 (1989) (Abstract for EP283959).
Yamatani et al., Chemical Abstracts, vol. 73, No. 131029 and 131031 (1970).

Primary Examiner—Cecilia Shen
Assistant Examiner—F. Bernhardt
Attorney, Agent, or Firm—Gordon W. Hueschen

[57] ABSTRACT

Heterocyclic dihydroxyquinoxaline compounds having the formula

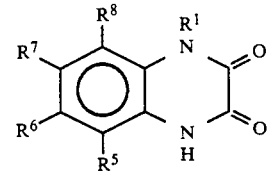

wherein
$R^1$ is $C_{1-12}$-alkyl, which may optionally be substututed by hydroxy, formyl, carboxy, carboxylic esters, amides or amines, $C_{3-8}$-cycloalkyl, aryl, aralkyl; and wherein $R^6$ is, hydrogen, halogen, CN, $CF_3$, $NO_2$, or OR', wherein R' is $C_{1-4}$-alkyl and $R^5$, $R^7$ and $R^8$ is hydrogen, provided $R^6$ is not $CF_3$, $OCH_3$, $NO_2$, Cl or Br when $R^1$ is $CH_3$; or $R^6$ and $R^7$ independently are $NO_2$, halogen, CN, $CF_3$, or OR', wherein R' is $C_{1-4}$-alkyl, and $R^5$ and $R^8$ are each hydrogen; or $R^5$ and $R^6$ together form a further fused aromatic ring, which may be substituted with halogen, $NO_2$, CN, $CF_3$ or OR', wherein R' is $C_{1-4}$-alkyl, and $R^7$ and $R^8$ independently are hydrogen, halogen, CN, $CF_3$, $NO_2$ or OR', wherein R' is $C_{1-4}$-alkyl; or $R^7$ and $R^8$ together form a further fused aromatic ring, which may be substituted with halogen, $NO_2$, CN, $CF_3$ or OR', wherein R' is $C_{1-4}$-alkyl, and $R^5$ and $R^6$ independently are hydrogen, halogen, CN, $CF_3$, $NO_2$ or OR', wherein R' is $C_{1-4}$-alkyl.

The invention also relates to a method of preparing the compounds, pharmaceutical compositions thereof, and their use.

The compounds are useful in the treatment of indications caused by hyperactivity of the excitatory neurotransmitters, particularly the quisqualate receptors, and especially as neuroleptics.

12 Claims, No Drawings

BENZO[F]QUINOXALINE-2,3(1H,4H)-DIONES

This is a continuation of application Ser. No. 268,939, filed Nov. 8, 1988, now U.S. Pat. No. 4,948,749, issued Aug. 14, 1990.

The present invention relates to therapeutically active heterocyclic compounds, a method Of preparing the same, pharmaceutical compositions comprising the compounds, and a method of treating therewith.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases Thus, known antagonists of excitatory amino acids have shown potent antiepileptic and muscle relaxant properties (A. Jones et al., Neurosci. Lett. 45, 157–61 (1984) and L. Turski et al., Neurosci. Lett. 53, 321–6 (1985)).

It has been suggested that accumulation of extracellular excitatory and neurotoxic amino acids, followed by hyperstimulation of neurons may explain the neuronal degenerations seen in neurological diseases as Huntingtons chorea, Parkinsonism, epilepsia, senile dementia, and deficiencies of mental and motoric performance seen after conditions of brain ischemia, anoxia and hypoglycemia (E. G. McGeer et al., Nature, 263, 517–19 (1976) and R. Simon et al., Science, 226, 850–2 (1984).

Excitatory amino acids exert their actions via specific receptors located postsynaptically or presynaptically. Such receptors are at present conveniently subdivided into three groups based on electrophysiological and neurochemical evidence: 1 the NMDA (N-methyl-D-aspartate) receptors, 2 the quisqualate receptors, and 3 the kainate receptors. L-glutamic acid and L-aspartic acid probably activate all the above types of excitatory amino acid receptors and possibly other types as well.

The consequence of excitatory amino acid interaction with postsynaptic receptors is an increase in intracellular cGMP levels (G. A. Foster et al., Life Sci. 27, 215–21 (1980)) and an opening of $Na^+$—channels (A. Luini et al., Proc. Natl. Acad. Sci. 78, 3250–54 (1981)). $Na^+$—influx in the neurons will depolarize the neuronal membranes, initiate an action potential and ultimately lead to a release of transmitter substance from the nerve terminal The effects of test compounds on the above mentioned secondary responses to receptor interaction can be tested in simple in vitro systems.

The above mentioned classification of excitatory amino acid receptors into NMDA, quisqualate, and kainate receptors is based primarily on the following electrophysiological and neurochemical findings.

(1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g., 2-amino-5-phosphono-valeric acid (D-APV) and 2-amino-7-phosphonoheptanoic acid (D-APH), while moderate antagonist activity is shown by the D-isomers of long chain 2-amino dicarboxylic acids (e.g.,D-2-amino-adipic acid) and long chain diaminodicarboxylic acids (e.g., diaminopimelic acid). The NMDA-induced synaptical responses have been extensively investigated in the mammalian CNS, especially in the spinal cord (J. Davies et al., J. Physiol. 297, 621–35 (1979) and the responses have been shown to be strongly inhibited by $Mg^{2+}$.

(2) Quisqualate receptors are activated selectively by quisqualic acid, other potent agonists being AMPA (2-amino-3-hydroxy-5-methyl-4-isoxazolepropionic acid) and L-glutamic acid. Glutamic acid diethyl ester (GDEE) is a selective but very weak antagonist of this site. Quisqualate receptors are relatively insensitive to $Mg^{2+}$.

It is well known that an excitatory aminoacid projection from prefrontal cortex to nucleus accumbens (a special part of the forebrain having dopamine neurons) exists (Christie et al., J. Neurochem. 45, 477–82 (1985)). Further it is well known that glutamate modulates the dopaminergic transmission in the striatum (Rudolph et al., Neurochem.int. 5, 479–86 (1983)) as well as the hyperactivity connected with presynaptic stimulation of the dopamine system with AMPA in nucleus accumbens (Arnt. Life Sci. 28, 1597–1603 (1981)).

Quisqualate antagonists are therefore useful as a new type of neuroleptic.

(3) Kainate receptors. Excitatory responses to kainic acid are relatively insensitive to antagonism by NMDA-antagonists and by GDEE, and it has been proposed that kainic acid activates a third subclass of acidic amino acid receptor Certain lactonized derivatives of kainic acid are selective antagonists (O. Goldberg et al., Neurosci. Lett. 23, 187–91 (1981)) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essense, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

Quisqualate receptor binding may be studied by using $^3H$-AM-PA as radioligand.

The influence of glutamic acid analogues on secondary effects of glutamate receptor interactions, such as on c-GMP formation and on $Na^+$—efflux, may be studied in vitro by using brain slices. Such experiments will provide information as to the efficacies (agonist/antagonist) of the test substances. This is in contrast to binding studies, which only provide information on the affinities of the compounds for the receptor.

The closest prior art is considered to be found in: J.Med.Chem. 28(3) 363–6 (1985) which for example discloses 6-methoxy-1-methyl-quinoxaline-2,3(1H,4H)-dione and J.Chem. Soc. 1170 (1962) which for example discloses 6-Bromo-1-methyl-quinoxaline-2,3(1H,4H)-dione.

It has now been found that the heterocyclic compounds of the invention have affinity for the quisqualate receptors and are antagonists in connection with this type of receptor which makes them useful in the treatment of any of the numerous indications caused by hyperactivity of excitatory amino acids and more specifically as neuroleptics.

The heterocyclic compounds of the invention have the general formula I

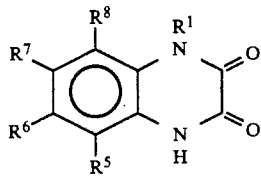

wherein
- $R^1$ is $C_{1-12}$-alkyl, which may obtionally be substituted by hydroxy, formyl, carboxy, carboxylic esters, amides or amines, $C_{3-8}$-cycloalkyl, aryl, aralkyl; and wherein $R^6$ is, hydrogen, halogen, CN, $CF_3$, $NO_2$, or OR', wherein R' is $C_{1-4}$-alkyl and $R^5$, $R^7$ and $R^8$ is hydrogen, provided $R^6$ is not $CF_3$, $OCH_3$, $NO_2$, CL or Br when $R^1$ is $CH_3$; or
- $R^6$ and $R^7$ independently are $NO_2$, halogen, CN, $CF_3$, or OR', wherein R' is $C_{1-4}$-alkyl, and $R^5$ and $R^8$ are each hydrogen; or
- $R^5$ and $R^6$ together form a further fused aromatic ring, which may be substituted with halogen, $NO_2$, CN, $CF_3$ or OR', wherein R' is $C_{1-4}$-alkyl, and $R^7$ and $R^8$ independently are hydrogen, halogen, CN, $CF_3$, $NO_2$ or OR', wherein R' is $C_{1-4}$-alkyl; or
- $R^7$ and $R^8$ together form a further fused aromatic ring, which may be substituted with halogen, $NO_2$, CN, $CF_3$ or OR', wherein R' is $C_{1-4}$-alkyl, and $R^5$ and $R^6$ independently are hydrogen, halogen, CN, $CF_3$, $NO_2$ or OR', wherein R' is $C_{1-4}$-alkyl.

The invention also relates to a method of preparing the above-mentioned compounds. This method comprises (a) reacting a compound having the formula II

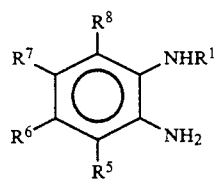

wherein $R^1$ and $R^2$ have the meanings set forth above, with oxalate or a reactive derivative thereof to form a compound of formula I, or (b) nitrating a compound having the formula III

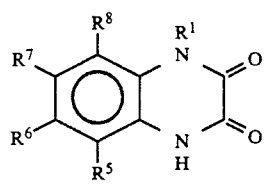

wherein $R^1$ has the meaning set forth above, and at least one of $R^5$, $R^6$, $R^7$, and $R^8$ is hydrogen and the others have the meanings defined above, to form a compound of formula I, or (c) reducing a compound having the formula IV

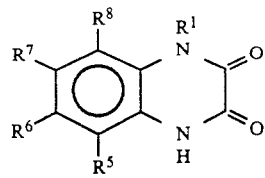

wherein $R^1$ has the meaning set forth above, and at least one of $R^5$, $R^7$ and $R^8$ is nitro and the others have the meanings defined above, to form a compound of formula I, or (d) reducing a compound having the formula V

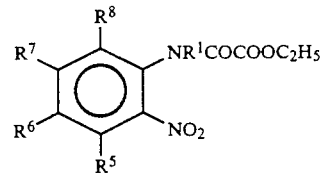

wherein $R^1$, $R^5$, $R^6$, $R^7$ and $R^8$ have the meanings set forth above, to form a compound of formula I.

The pharmacological properties of the compounds of the present invention can be illustrated by determining their capability for displacing radioactively labelled 2-amino-3-hydroxy-5-methyl-4-isoxazolepropionic acid (AMPA) from the quisqualate type receptors. The antagonistic properties of the compounds is demonstrated by their capability to antagonize quisqualic acid stimulated $^3$H-GABA-efflux from cultured rat cortical neurones.

The displacement activity of the compounds may be shown by determining the $IC_{50}$ value which represents the concentration ($\mu$g/ml) which causes a displacement of 50% of the specific binding of $^3$H-AMPA.

The antagonism is measured by determining the $EC_{50}$ value which represents the concentration which reduces the rate of quisqualic acid stimulated $^3$H-GABA efflux by 50%.

$^3$H-AMPA binding

500 $\mu$l of thawed rat cerebral cortical membrane homogenate in Tris-HCl (30 mM), $CaCl_2$ (2.5 mM) and KSCN (100 mM) pH 7.1 were incubated at 0° C. for 30 min. with 25 $\mu$l $^3$H-AMPA (5 nM final concentration) and the test compound and buffer. Nonspecific binding was determined by incubation with L-glutamic acid (600 $\mu$M final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Cell cultures

Cerebral cortices of 16 day old mouse embryos are chopped in 0.4×0.4 mm cubes. The tissue is dissociated by mild trypsinization (0.1% (wt/vol) trypsin, 37° C., 15 min) and subsequently inoculated into poly-L-lysine-coated 3 cm Petri dishes containing a slightly modified DMEM (24.5 mM KCl, 30 mM glucose) supplemented with p-aminobenzoate 7 $\mu$M), insulin (100, $\mu$/l) and 10% (vol/vol) horse serum. Cells are maintained in culture for 5-7 days with the addition of the antimitotic agent cytosine arbinoside (40 μM) from day 2 in vitro to prevent glial proliferation For further details and references see Drejer et al. (Exp. Brain Res. 47, 259 (1982)).

Release experiments

Release experiments are performed using the model described by Drejer et al. (Life Sci. 38, 2077 (1986)). Cerebral cortex interneurons cultured in Petri dishes (30 mm) are added 100 μM gamma-vinyl-GABA one hour before the experiment in order to inhibit degradation of GABA in the neurons. 30 min. before the experiment 5 μCi $^3$H-GABA is added to each culture and after this preloading period the cell monolayer at the bottom of the dish is covered with a piece of nylon mesh to protect the cells against mechanical damage and to facilitate dispersion of medium over the cell layer. The preloading medium is removed and the Petri dishes are placed in a superfusion system. This system consists of a peristaltic pump continuously delivering thermostated 37° C. superfusion medium (HEPES buffered saline (HBS): 10 mM HEPES, 135 mM NaCl, 5 mM KCl, 0.6 mM MgSO$_4$, 1.0 mM CaCl$_2$ and 6 mM D-glucose; pH 7.4) from a reservoir to the top of the slightly tilted Petri dish. The medium is continuously collected from the lower part of the dish and delivered to a fraction collector. Initially, the cells are superfused with HBS for 15 min. (flow rate 2 ml/min.). The cells are stimulated for 30 sec. every 4 min. by changing the superfusion medium from HBS to a corresponding medium containing quisqualate and test compound. The release of $^3$H-GABA in the presence of quisqualate (stimulated release in cpm) are corrected for the mean basal release (Cpm) before and after the stimulation.

Test results obtained by testing some compounds employed in the present invention will appear from the folowing table 1.

TABLE 1

|  | IC$_{50}$ μg/ml | EC$_{50}$ μg/ml |
| --- | --- | --- |
| Compound 7 | 0.96 | 2.1 |
| Compound 16 | 0.69 | — |
| Compound 13 | 0.42 | 2.1 |
| Compound 27k | 0.61 | >4 |

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fattY acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or.is desired.

Generally, the compounds of this invention are dispensed in unit dosage form comprising 50–200 mg of active ingredient in or together with a pharmaceutically-acceptable carrier per unit dosage.

The dosage of the compounds according to this invention is 1–500 mg/day. e.g. about 100 mg per dose when administered to patients, e.g., humans, as a drug.

A typical tablet which may be prepared by conventional tabletting techniques contains:

| | | |
| --- | --- | --- |
| Core: | | |
| Active compound (as free compound or salt thereof) | | 100 mg |
| Colloidal silicon dioxide (Aerosil ®) | | 1.5 mg |
| Cellulose, microcryst. (Avicel ®) | | 70 mg |
| Modified cellulose gum (Ac-Di-Sol ®) | | 7.5 mg |
| Magnesium stearate | | 1 mg |
| Coating: | | |
| HPMC | approx. | 9 mg |
| *Mywacett ® 9-40 T | approx. | 0.9 mg |

*Acylated monoglyceride used as plasticizer for film-coating

The free quinoxaline compounds of the present invention which form alkali metal or alkaline earth metal salts may be employed in such salt form. Such alkali metal or earth alkali metal salts are ordinarily formed by reacting the quinoxaline compound with an equivalent amount or excess of the selected alkali metal or earth alkali metal as the hydroxide, frequently and suitably by admixture in the presence of a neutral solvent, from which the salt may be precipitated or recovered in other conventional manner, e.g., by evaporation. Administration of a compound of the invention is often preferably in the form of a pharmaceutically-acceptable water-soluble alkali metal or earth alkali metal salt thereof, and orally, rectally, or parenterally in the form of a pharmaceutical composition wherein it is present together with a pharmaceutically-acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective neuroleptic especially quisqualate antagonistic, amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of neuroleptic, particularly quisqualate antagonistic, activity and their low toxicity, together presenting a most favorale therapeutic index, the compounds of the invention may be administered to a subject, e.g., a living animal body, in need of such neuroleptic treatment, elimination, alleviation, or amelioration of an indication which is sensitive to a change in the quisqualate receptor condition, often preferably in the form of an alkali metal or earth alkali metal salt thereof, concurrently, simultaneously, or together with a pharmaceutically-acceptable carrier or diluent, especially and preferably in the form of a pharmaceutical composition thereof, whether by oral, rectal, or parenteral (including subcutaneous) route, in an effective amount. Suitable dosage ranges are 50–200 milligrams daily, preferably 50–100 milligrams daily, and especially 70–100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to hyperactivity of the excitatory neurotransmitters, and particularly the quisqualate receptors, in a subject in need thereof, which comprises the step of administering to the said subject a neurologically- or neuroleptically-effective amount of a quisqualate antagonistic quinoxaline compound of the invention.

The invention will now be described in further detail with reference to the following examples.

EXAMPLE 1 a. N-Cyclohexyl-2,4-dinitroaniline

To a solution of 2.50 g (25,3 mmol) cyclohexylamine in 100 ml dry dimethylformamide was added 2.55 g (25,1 mmol) dry triethylamine. A solution of 4.65 g (25,0 mmol) 2.4-dinitro-1-fluorobenzen in 20 ml dry dimethylformamide was added dropwise and the reaction mixture was stirred at 25° for 1 h. The mixture was evaporated and then stirred with water to give 6.1 g (92%). N-cyclohexyl-2,4-dinitroaniline. M.p. 153.2° C.

b. N-cyclohexyl-2-amino-4-nitroaniline

A mixture of 2.2 g (8,3 mmol) N-cyclohexyl-2,4-dinitroaniline, 1.95 g (36.4 mmol) ammonium chloride, 7.85 g (32.7 mmol) sodium sulfide hydrate and 100 ml methanol was refluxed for 1 h. After cooling to 25° C. the mixture was filtered and evaporated The product was stirred with water to give 1.6 g (82%) N-cyclohexyl-2-amino-4-nitroaniline. $^1$H-NMR (CDCl$_3$): 7.9–7.4 (2H, m), 6.5 (1H, d), 4.4 (1H, broad s), 3.4 (2H, broad s), 2.3–0.8 (11H, m).

c. 1-Cyclohexyl-6-nitroquinoxaline-2,3(1H,4H)-dione (Compound 1)

A mixture of 0.9 g (3.1 mmol) N-cyclohexyl-2-amino-4-nitroaniline and 1.0 g (7.9 mmol) oxalic acid dihydrate in 50 ml 4 N hydrochloric acid was refluxed for 5 h. After cooling to 25° C. the product was filtered off. The crude product was recrystallized (ether-water) to give 0.2 g (19%) 1-cyclohexyl-6-nitroquinoxaline-2,3(1H,4H)-dione. M.p. (DSC): decomp. $^1$H-NMR (DMSO-d$_6$): 12.2 (1H, broad s), 8.1–7.7 (3H, m), 3.0–1.0 (11H, m).

EXAMPLE 2 a. N-Benzyl-2,4-dinitroaniline

To a solution of 2.68 g (25.0 mmol) benzylamine in 100 ml dry dimethylformamide was added 2.55 g (25.2 mmol) dry triethylamine. A solution of 4.65 g (25.0 mmol) 2,4-dinitro-1-fluorbenzen in 20 ml dry dimethylformamide was added dropwise, and the reaction mixture was stirred at 25° C. for 1 h. The mixture was evaporated, then dissolved in 50 ml ethylacetate and washed with 100 ml water. The ethyl acetate was evaporated to give 6.1 g (89%) N-benzyl-2,4-dinitroaniline. M.p. 106.2° C. $^1$H-NMR (CDCl$_3$): 9.1 (1H, d), 8.9 (1H, broad s), 8.2 (1H, dd), 7.3 (5H, s), 6.9 (1H, d), 4.2 (2H, d).

b. N-Benzyl-2-amino-4-nitroaniline

A mixture of 2.0 g (7.3 mmol) N-benzyl-2,4-dinitroaniline, 1.50 g (28.0 mmol) ammonium chloride, 6.7 g (28.0 mmol) sodium sulfide hydrate and 100 ml methanol was refluxed for ¾ h. After cooling to 25° C. the mixture was filtered and evaporated. The product was stirred with water to give 1.3 g (73%) N-benzyl-2-amino-4-nitroaniline. $^1$H-NMR (CDCl$_3$): 8.1–6.5 (8H, m), 4.9–4.3 (3H, m), 3.4 (2H, broad s).

c. 1-Benzyl-6-nitroquinoxaline-2,3(1H,4H)-dione (Compound 2)

A mixture of 0.5 g (2.1 mmol) N-benzyl-2-amino-4-nitroaniline and 0.55 g (4.4 mmol) oxalic acid dihydrate in 30 ml 4N hydrochloric acid was refluxed for 5 h. After cooling to 25° C. the product was filtered off and washed with water. The crude product was recrystallized (dimethylformamide-water), washed with 10 ml water, 5 ml ethanol and 5 ml ether to give 0.3 g (49%) 1-benzyl-6-nitroquinoxaline-2,3(1H,4H)-dione. M.p. (DSC): 292.2° C. $^1$H-NMR (DMSO-d$_6$): 12.4 (1H, broad s), 8.2–7.0 (8H, m), 5.4 (2H, s).

EXAMPLE 3

6-Methoxy-1-methyl-7-nitroquinoxaline-2,3-(1H,4H)-dione (Compound 3)

To a solution of 0.2 g (0.97 mmol) 6-methoxy-1-methylquinoxaline-2,3(1H,4H)-dione in 10 ml concentrated sulfuric acid was added at 0° C. 0.1 g (0.99 mmol) potassium nitrate. Stirring was continued at 0° C. for 30 min., and then at 25° C. for 1 h. The reaction mixture was poured into 50 ml ice-water to give a precipitate Recrystallization (dimethylformamide-water) of the crude product gave 0.15 g (62%) 6-methoxy-1-methyl-7-nitroquinoxaline-2,3(1H,4H)-dione. M.p. 356° C. NMR (DMSO-d$_6$): 12.0 (1H, broad s), 7.77 (1H, s), 3.90 (3H, s), 3.47 (3H, s).

EXAMPLE 4 a. N-Methyl-1-acetamido-4-methoxy-2-nitrobenzene

A solution of 2.0 g (9.6 mmol) 1-acetamido-4-methoxy-2-nitrobenzene in 16 ml dry dimethylformamide was added gradually at +10° C. to a stirred suspension of 0.4 g (9.7 mmol) 55–60% sodium hydride in 32 ml dry dimethylformamide. Stirring was continued at +10° C. for 20 min, and then 2.0 ml (32 mmol) methyl iodide was added. Stirring was continued at +10° C. for another 1 h, and then the reaction mixture was evaporated in vacuo. The residue in 100 ml ethyl acetate was washed with water (2×50 ml). The ethyl acetate phase was dried and evaporated in vacuo to give an oil (1.8 g). NMR (CDCl$_3$): 7.6–7.2 (3H), 3.87 (3H, s), 3.17 (3H, s), 1.83 (3H, s).

b. N-Methyl-4-methoxy-2-nitroaniline

A mixture of 1.6 g (7.2 mmol) N-methyl-1-acetamido-4-methoxy-2-nitrobenzene in 20 ml concentrated hydrochloric acid and 20 ml water and 30 ml ethanol was refluxed for 3 h. The reaction mixture was cooled to 0° C., and the precipitate was filtered off and washed with water to give 1.0 g (81%) N-methyl-4-methoxy-2-nitroaniline. M.p. 93°–94° C.

c. 6-Methoxy-1-methylquinoxaline-2,3(1H,4H)-dione (Compound 4)

A solution of 0.75 g (4.1 mmol) N-methyl-4-methoxy-2-nitroaniline in 150 ml ethanol was hydrogenated at atm. pressure by using 5% Pd-C (0.1 g) as a catalyst. The reaction mixture was filtered, added 2 ml 1N hydrochloric acid and then evaporated in vacuo to give 2-amino-4-methoxy-N-methylaniline as crystals.

A mixture of the crude product and 1 g oxalic acid dihydrate in 50 ml 4N hydrochloric acid was refluxed for 3 h. After cooling to 25° C., the precipitate was filtered off and washed with water. The crude product was recrystallized (dimethylformamide) to give 0.43 g (51%) 6-methoxy-1-methyl-quinoxaline-2,3-(1H,4H)-dione. M.p. 332° C. NMR (DMSO-d$_6$): 11.7 (1H, broad s), 7.1–6.4 (3H), 3.73 (3H, s), 3.47 (3H, s).

EXAMPLE 5 a. N-Methyl-1-acetamido-5-methoxy-2-nitrobenzene

A solution of 5.75 g (27.4 mmol) 1-acetamido-5-methoxy-2-nitrobenzene in 75 ml dry dimethylformamide was added gradually at +10° C. to a stirred suspension of 1.15 g (ca. 28 mmol) 55–60% sodium hydride in 50 ml dry dimethylformamide. Stirring was continued at +10° C. for 20 min., and then 5.8 ml (94 mmol) methyl iodide was added. Stirring was continued at +10° C. for another 1 h, and then the reaction mixture was evaporated in vacuo. The residue in 150 ml ethyl acetate was washed with water (2×50 ml). The ethyl acetate phase was dried and evaporated in vacuo to give an oil (6 g, 97%).

b. N-Methyl-5-methoxy-2-nitroaniline

A mixture of 6 g (26.8 mmol) N-methyl-1-acetamido-5-methoxy-2-nitrobenzene in 80 ml concentrated hydrochloric acid and 80 ml water and 40 ml ethanol was refluxed for 2 h. The reaction mixture was cooled to 0° C., and the precipitate was filtered off and washed with water to give 3.94 (82% of N-methyl-5-methoxy-2-nitroaniline. M.p. 117°–118° C.

c. 7-Methoxy-1-methylquinoxaline-2,3(1H,4H)-dione (Compound 5)

A solution of 3.7 g (20.4 mmol) N-methyl-5-methoxy-2-nitroaniline in 700 ml ethanol was added 7.4 ml 4N hydrochloric acid, and then hydrogenated at atm. pressure by using 5% Pd-C (0.5 g) as a catalyst. The reaction mixture was filtered and evaporated in vacuo to give 2-amino-5-methoxy-N-methylaniline as crystals.

A mixture of the crude product and 6 g oxalic acid dihydrate in 75 ml 4N hydrochloric acid was refluxed for 3 h. After cooling to 25° C., the precipitate was filtered off and washed with water. The crude product was recrystallized (dimethylformamide-water) to give 3.4 g (81%) 7-methoxy-1-methylquinoxaline-2,3 (1H,4H)-dione. M p. 310° C. NMR (DMSO-d$_6$): 11.8 (1H, broad s), 7.1 (1H, d) 6.87 (1H, s), 6.8 (1H, d), 3.83 (3H, s), 3.5 (3H, s).

EXAMPLE 6

7-Methoxy-1-methyl-6-nitroquinoxaline-2,3(1H,4H)-dione (Compound 6)

To a solution of 0.5 g (2.4 mmol) 7-methoxy-1-methylquinoxaline-2,3(1H,4H)-dione in 20 ml concentrated sulfuric acid was added at 0° C. 0.25 g (2.48 mmol) potassium nitrate. Stirring was continued at 0° C. for 30 min, and then at 25° C. for 90 min. The reaction mixture was poured into 100 ml ice-water to give 0.51 g (84% of 7-methoxy-1-methyl-6-nitroquinoxaline-2,3(1H,4H)-dione as a precipitate. M.p. 343° C. NMR (DMSO-d$_6$): 11.9 (1H, broad s), 7.67 (1H, s), 7.0 (1H, s), 3.97 (3H, s), 3.53 (3H, s).

EXAMPLE 7

1-Methyl-6-nitroquinoxaline-2,3(1H,4H)-dione (Compound 7)

A mixture of 1.0 g (5.9 mmol) 2-amino-4-nitro-N-methylaniline and 1.5 g (11.9 mmol) oxalic acid dihydrate in 50 ml 4N hydrochloric acid was refluxed for 3 h. After cooling to 25° C., the precipitate was filtered off and washed with water. The crude product was recrystallized (dimethylformamide-water) to give 1.0 g (78%) of 1-methyl-6-nitroquinoxaline-2.3-(1H,4H)-dione. M.p. 356° C. NMR (DMSO-d$_6$): 12.2 (1H, broad s), 7.9 (1H, d), 7.8 (1H, s), 7.4 (1H, d), 3.47 (3H, s).

EXAMPLE 8

1-Methyl-6,7-dinitroquinoxaline-2,3(1H,4H)-dione (Compound 8)

To a solution of 0.5 g (2.3 mmol) 1-methyl-6-nitroquinoxaline-2,3(1H,4H)-dione in 15 concentrated sulfuric acid was added at 0° C. 0.27 g (2.7 mmol) potassium nitrate. Stirring was continued at 0° C. for 30 min, and then at 25° C. for 20 h. The reaction mixture was poured into 70 ml ice-water.

The precipitate was filtered off and washed with water to give 0.49 g (82%) of 1-methyl-6,7-dinitroquinoxaline-2,3-(1H,4H)-dione. M.p. 370–380° C. NMR (DMSO-d$_6$): 12.5 (1H, broad s), 8.0 (1H, s), 7.73 (1H, s), 3.5 (3H, s).

EXAMPLE 9

6-Amino-1-methylquinoxaline-2,3(1H,4H)-dione hydrochloride (Compound 9)

A solution of 0.5 g (2.3 mmol) 1-methyl-6-nitroquinoxaline-2,3(1H,4H)-dione in 25 ml dimethylformamide was hydrogenated at atm. pressure by using 5% Pd-c (0.1 g) as a catalyst. The reaction mixture was added 1 ml 4N hydrochloric acid, filtered and evaporated in vacuo. The residue was stirred with ethyl acetate. The precipitate was filtered off to give 0.5 g (98%) of 6-amino-1-methyl-quinoxaline-2,3(1H,4H)-dione hydrochloride. NMR (DMSO-d$_6$+D$_2$O): 7.3 (1H, d), 7.13 (1H, s), 7.1 (1H, d), 3.5 (3H, s), 2.6 (3H, s).

EXAMPLE 10

6-Acetamido-1-methylquinoxaline-2,3(1H,4H)-dione (Compound 10)

To a solution of 0.3 g (1.3 mmol) 6-amino-1-methylquinoxaline-2,3(1H,4H)-dione in a mixture of 15 ml water and 0.6 ml 4N sodium hydroxide was added 5 ml acetic acid anhydride. Stirring was continued at 25° C. for 2 h. The precipitate was filtered off and washed with water to give 0.21 g (68%) of 6-acetamido-1-methylquinoxaline-2,3(1H,4H)-dione. M.p. 390° C. NMR (DMSO-$d_6$): 10.1 (1H, broad s), 9.7 (1H, broad s), 7.5–7.0 (3H), 3.43 (3H, s), 2.0 (3H, s).

EXAMPLE 11 a. N-Methyl-1-acetamido-4,5-dimethoxy-2-nitrobenzene

A solution of 1.5 g (6.3 mmol) 1-acetamido-4,5-dimethoxy-2-nitrobenzene in 30 ml dry dimethylformamide was added gradaully at 25° C. to a stirred and ice-cooled suspension of 0.3 g (7.3 mmol) 55–60% sodium hydride in 15 ml dry dimethylformamide. Stirring was continued at 0° C. for 15 min., and then 1.5 ml (24 mmol) methyl iodide was added. Stirring was continued at 0° C. for 1 h, and then the reaction mixture was evaporated in vacuo. The residue in 100 ml ethyl acetate was washed with water (2×50 ml). The ethyl acetate phase was dried and evaporated in vacuo to give 1.2 g (75%) N-methyl-1-acetamido-4,5-dimethoxy-2-nitrobenzene as yellow crystals. NMR (DMSO-$d_6$): 7.5 (1H, s), 7.07 (1H, s), 3.83 (6H, s), 3.0 (3H, s), 1.7 (3H, s).

b. N-Methyl-4,5-dimethoxy-2-nitroaniline

A mixture of 1 g (3.9 mmol) N-methyl-1-acetamido-4-methoxy-2-nitrobenzene in 10 ml concentrated hydrochloric acid and 10 ml water and 15 ml ethanol was refluxed for 2 h. The reaction mixture was cooled to 0° C. and added 25 ml water. The precipitate was filtered off and washed with water to give 0.45 g (54%) N-methyl-4,5-dimethoxy-2-nitroaniline. M.p. 147.1° C.

c. 6,7-Dimethoxy-1-methylquinoxaline-2,3(1H,4H)-dione (Compound 11)

A solution of 0.5 g (2.4 mmol) N-methyl-4,5-dimethoxy-2-nitroanilin in 150 ml ethanol was added 1 ml 4N hydrochloric acid, and the mixture was hydrogenated at atm. pressure by using 5% Pd-C (0.1 g) as a catalyst. The reaction mixture was filtered and evaporated in vacuo to give 2-amino-4.5-dimethoxy-N-methylaniline.

A mixture of the crude product and 0.7 g oxalic acid dihydrate in 25 ml 4N hydrochloric acid was refluxed for 3 h. After cooling to 25° C., the reaction mixture was evaporated in vacuo. The residue was stirred with methanol (25 ml). The precipitate was filtered off and washed with methanol and ether to give 0.25 g (40%) 6,7-dimethoxy-1-methylquinoxaline-2,3(1H,4H)-dione. M.p. 308° C. NMR (DMSO-$d_6$): 11.7 (1H, broad s), 6.8 (1H, s), 6.7 (1H, s), 3.8 (3H, s), 3.7 (3H, s), 3.5 (3H, s).

EXAMPLE 12 a. 4-Methylamino-3-nitrobenzotrifluoride

A stream of methylamine was bubbled through a solution of 1.3 g (6.2 mmol) 4-fluoro-3-nitrobenzotrifluoride in 25 ml dimethylformamide at 25° C. for 5 min. Stirring was continued at 25° C. for 2 h, and then the reaction mixture was evaporated in vacuo. The residue was stirred with water, and the precipitate was filtered off to give 1.17 g (86%) 4-methylamino-3-nitrobenzotrifluoride. NMR (CDCl$_3$): 8.4 (1H, s), 8.2 (1H, broad s), 7.6 (1H, dd), 6.9 (1H, d), 3.1 (3H, d).

b. 1-Methyl-6-trifluoromethylquinoxaline-2,3(1H,4H)-dione (Compound 12)

A solution of 1.1 g (5.0 mmol) 4-methylamino-3-nitrobenzotrifluoride in 200 ml ethanol was hydrogenated at atm. pressure by using 5% Pd-C (0.15 g) as a catalyst. The reaction mixture was filtered and evaporated in vacuo to give 3-amino-4-methylaminobenzotrifluoride as crystals.

A solution of the crude product in 75 ml dry tetrahydrofuran was added 1.5 ml (10.9 mmol) dry triethylamine, and then a solution of 1.2 ml (10.7 mmol) ethoxalylchloride in 25 ml dry tetrahydrofuran was added dropwise. Stirring was continued at 25° C. for 1 h. The reaction mixture was filtered and evaporated in vacuo to give an oil. The crude product in 50 ml 1N hydrochloric acid and 10 ml ethanol was refluxed for 2 h. After cooling to 25° C., the precipitate was filtered off, and recrystallized (dimethylformamide-water) to give 0.6 g (50%) 1-methyl-6-trifluoromethylquinoxaline-2,3(1H,4H)-dione, M.p. 255° C. NMR (DMSO-$d_6$): 12.1 (1H, broad s), 7.5 (3H, m), 3.53 (3H, s).

EXAMPLE 13 a. 6-Bromo-2-methoxy-1-nitronaphthalene

An ice-cooled solution of 100% nitric acid (12.0 ml, 0.27 mol) in 95 ml of acetic anhydride was added dropwise to a solution of 6-bromo-2-methoxynaphthalene (61.7 g, 0.26 mol) and 0.25 ml of conc. sulfuric acid in 570 ml of acetic anhydride while maintaining the temperature at +30° to +40° C. The mixture was stirred for an additional 10 min. and filtered. The solid was washed with water and dried to give 60.0 g (73%) of the nitro compound. M.p. 151–152° C., $^1$H-NMR (CDCl$_3$): 3.98 (s, 3H, CH$_3$), 7.16–7.93 (m, 5H, ArH).

b. 6-Bromo-2-methylamino-1-nitronaphthalene

A solution of 6-bromo-2 methoxy-1-nitronaphthalene (5.64 g, 20 mmol) in 100 ml of dry N,N-dimethylformamide saturated with methylamine was stirred in a stoppered flask at 80° C. for 4 h. During the reaction period the mixture was saturated twice with a further quantity of methylamine. The cooled mixture was poured into 1 l of ice/water. After stirring for 1 h, the orange solid was collected by filtration and washed with water, and dried in vacuo over phosphorus pentoxide affording 5.43 g (96%) of the title compound. M.p. 169°–170° C.; $^1$H-NMR (CDCl$_3$): 3.11 (d, J=5 Hz, 3H, CH$_3$), 7.00 (d, J=9 Hz, 1H, ArH), 7.45–7.78 (m, 3H, ArH), 8.60 (d, J=9 Hz, 1H, ArH), 8.7 (broad, 1H, NH).

c. 4-Methylbenzo[f]quinoxaline-2,3(1H,4H)-dione (Compound 13)

A suspension of 6-bromo-2-methylamino-1-nitronaphthalene (2.81 g, 10 mmol) and triethylamine (1.40 ml, 10 mmol) in 150 ml of 96% ethanol was hydrogenated at room temperature and atmospheric pressure in the presence of 5% palladiumon-carbon (500 mg) for 1 h. The solution was filtered directly into 50 ml of 4M hydrochloric acid under a nitrogen atmosphere. The acidic filtrate was evaporated to dryness and the solid diaminonaphthalene hydrochloride was refluxed with oxalic acid dihydrate (1.5 g, 11.9 mmol) in 25 ml of 4M hydrochloric acid withoutfurther purification. After reflux for 2 h the mixture was cooled, and the solid product was isolated by filtration and washed with water, ethanol and ether to give 2.07 g (92%) of the title compound. M.p. 332.7° C. (ethanol); IR (KBr): 1685 cm.$^{-1}$; $^1$H-NMR (DMSO-d$_6$): 3.60 (s, 3H, CH$_3$), 7.33–7.93 (m, 5H, ArH), 8.37–8.60 (m, 1H, ArH), 12.13 (broad s, 1H, NH); MS m/z: 226 (M+, 100%).

In exactly the same manner 4-cyclohexylbenzo[f]quinoxaline-2,3(1H,4H)-dione was made from 6-bromo-2-cyclohexylbenzo[f]quinoxaline. M.p. 288° C. (Compound 27k).

EXAMPLE 14

6-Chloro-1-methylquinoxaline-2,3(1H,4H)-dione (Compound 14)

A suspension of 4-chloro-1-methylamino-2-nitrobenzene (1.73 g, 9.3 mmol) in 50 ml of ethanol was hydrogenated at room temperature and 2 atm. pressure in the presence of 5% palladium-on-carbon (0.5 g) until the theoretical amount of hydrogen was absorbed. The catalyst was filtered off, and 50 ml of 1N hydrochloric acid was added to the filtrate. The acidic filtrate was evaporated to dryness and the solid residue was refluxed with oxalic acid dihydrate (1.4 g, 11 mmol) in 100 ml of 4M hydrochloric acid for 90 min. The mixture was cooled and the precipitated product was collected by filtration and washed with water, ethanol and ether to give 0.45 g (23%) of the title compound. M.p. 341.5° C. (N,N-dimethylformamide): IR (KBr): 1700, 1660 cm$^{-1}$, $^1$H-NMR (DMSO-d$_6$: 3.43 (s, 3H, CH$_3$), 6.97–7.40 (m, 3H, ArH), 12.0 (broad s, 1H, NH); MS m/z: 212 (M++2, 50%), 210 (M+, 100%).

EXAMPLE 15 a. N-Cyclohexyl-2-nitro-5-chloraniline

A mixture of 15.09 g (78 mmol) 2,4-dichloronitrobenzen, 7.7 g (78 mmol) cyclohexylamine, 7.9 g (78 mmol) triethylamine and 100 ml dimethylformamide was stirred at 80° C. for 3 h. After cooling to 25° C. the mixture was evaporated, dissolved in 200 ml ether and filtered. The ether solution was washed with water and evaporated to the half volume. The precipitate was filtered off to give 3.8 g (19%) N-cyclohexyl-2-nitro-5-chloraniline. M.p. 124.5° C. $^1$H-NMR (CDCl$_3$): 8.2 (2H, m), 6.8 (1H, d), 6.5 (1H, dd), 3.5 (1H, broad s), 2.4–0.8 (10H, m).

b. 1-Cyclohexyl-7-chlorquinoxaline-2,3(1H,4H)-dione (Compound 15)

3.6 g (14.1 mmol) N-cyclohexyl-2-nitroaniline was dissolved in 50 ml ethanol and 150 ml ethylacetate. The solution was hydroqenated at atm. pressure by using Ra-Ni (1 g) as a catalyst. The reaction mixture was filtered and the filtrate was evaporated to give an oil. A mixture of the oil and 3.5 g (28 mmol) oxalic acid dihydrate in 100 ml 4N hydrochloric acid was refluxed for 2 h. After cooling to 25° C. the product was filtered off and washed with water to give 3.4 g (86%) 1-cyclohexyl-7-chlorquinoxaline-2,3(1H, 4H)-dione. M.p. (DSC) 310.6° C. $^1$H-NMR (DMSO-d$_6$): 12.0 (1H, broad s), 7.7 (1H, s), 7.2 (2H, s), 4.2 (1H, broad, s) 2.0–1.0 (10H, m).

EXAMPLE 16

1-Cyclohexyl-6-nitro-7-chlorquinoxaline-2,3(1H,4H)-dione (Compound 16)

A solution of 3.1 g (11 mmol) 1-cyclohexyl-7-chlorquinoxaline-2,3(1H,4H)-dione in 100 ml concentrated sulfuric acid (95–97%) was ice-cooled and then added 1.1 g (11 mmol) potassium nitrate. Stirring was continued at 0° C. for 30 min. and then at 25° C. for 17 h. The reaction mixture was poured into 500 ml ice-water. The precipitate was filtered off and washed with water to give 3.0 g (82%) 1-cyclohexyl-6-nitro-7-chlorquinoxaline-2,3(1H,4H)-dione. M.p. (DSC): decomp. $^1$H-NMR (DMSO-d$_6$): 12.2 (1H, broad s), 7.9 (2H, s), 4.0–1.0 (11H, m).

EXAMPLE 17 a. N-Cyclohexyl-4-cyano-2-nitroaniline

To a solution of 3.0 g (16 mmol) 3-chloro-2-nitrobenzonitrile in 50 ml dimethylformamide was added 1.8 g (18 mmol) dry triethylamine and 1.8 g (18 mmol) cyclohexylamine. The reaction mixture was stirred at 80° C. for 1 h. After cooling to 25° C. 100 ml water was added, and the precipitate was filtered off. The crude product was recrystallized (methanol) to give 1.6 g (65%) N-cyclohexyl-4-cyano-2-nitroaniline. M.p. 109.0° C. $^1$H-NMR (CDCl$_3$): 8.4–6.8 (4H, m), 3.5 (1H, broad s), 2.4–1.0 (10H, m).

b. 1-Cyclohexyl-6-cyanoquinoxaline-2,3(1H,4H)-dione (Compound 17)

A solution of 1.2 g (4.9 mmol) N-cyclohexyl-4-cyano-2-nitroaniline in 100 ml ethyl acetate was hydrogenated at 40 psi by using 5% Pd/C (100 mg) as a catalyst. The reaction mixture was filtered and 2.0 g (20 mmol) dry triethylamine was added. A solution of 2.7 g (20 mmol) ethyl oxalyl chloride in 20 ml ethyl acetate was added dropwise and the reaction mixture was stirred for 3 h. The reaction mixture was filtered and evaporated in vacuo to give an oil. A mixture of the oil, 20 ml ethanol and 70 ml 0.5 N hydrochloric acid was refluxed for 1 h. After cooling to 25° C. the precipitate was filtered off and washed with water to give 0.33 g (25%) 1-cyclohexyl-6-cyanoquinoxaline-2.3(1H,4H)-dione. M.p. (DSC): decomp. $^1$H-NMR (DMSO-d$_6$): 12.0 (1H, broad s), 8.0–7.4 (3H, m), 4.4 (1H, m), 2.7–0.7 (10H, m). IR (KBr): 2450, 1700 cm$^{-1}$.

EXAMPLE 18 a. N-Cyclohexyl-4-fluoro-2-nitroaniline

A solution of 5.0 g (31 mmol) 2.5-difluoronitrobenzene, 3.8 ml (31 mmol) cyclohexylamine and 4.4 ml (31 mmol) triethylamine in 50 ml dimethylformamide was stirred at 80° C. for 2 h. After cooling to 25° C. 100 ml water was added. The precipitate was filtered off and washed with water to give 6.1 g (82%) N-cyclohexy-4-fluoro-2-nitroaniline. M.p. 93.0° C.

b. 1-Cyclohexyl-6-fluoroquinoxaline-2,3(1H,4H)-dione (Compound 18)

A solution of 2.0 g (8.4 mmol) N-cyclohexyl-4-fluoro-2-nitroaniline in a mixture of 100 ml ethanol and 50 ml ethyl acetate was hydrogenated at atm. pressure by using Ra-Ni (1 g) as a catalyst. The reaction mixture was filtered and evaporated in vacuo to give an oil. A mixture of the oil, 2.8 g (23 mmol) oxalic acid dihydrate, 10 ml ethanol and 150 ml 4N hydrochloric acid was refluxed for 1½h. After cooling to 25° C. the precipitate was filtered off and washed with water to give 1.1 g (50%) 1-cyclohexyl-6-fluoroquinoxaline-2,3(1H,4H)-dione. M.p. 289.8° C., 1H-NMR (DMSO-d$_6$): 12.0 (1H, broad s), 7.6 (1H, M), 7.0 (2H, M), 4.5 (1H, M), 2.6–0.9 (10H, M).

EXAMPLE 19 a. N-Cyclohexyl-2-nitro-4-trifluoromethylaniline

To a solution of 5.0 g (22 mmol) 4-chloro-3-nitrobenzotrifluoride in 100 ml dimethylformamide was added 3.4 ml (24 mmol) triethylamine and 2.8 ml (23 mmol) cyclohexylamine. The reaction mixture was stirred at 80° C. for 2 h. After cooling to 25° C. the reaction mixture was evaporated in vacuo. The residue was stirred with 100 ml water and the precipitate was filtered off. Recrystallization (methanol) gave 3.9 g (61%) N-cyclohexyl-2-nitro-4-trifluoromethylaniline. M.p. 80.1° C., $^1$H-NMR (CDCl$_3$): 8.4 (1H, s), 8.3 (1H, m), 7.5 (1H, dd), 6.9 (1H, d), 3.5 (1H, broad s).

b.
1-Cyclohexyl-6-trifluoromethylquinoxaline-2,3(1H,4H)-dione (Compound 19)

A solution of 2.1 g (7.3 mmol) N-cyclohexyl-2-nitro-4-trifluoromethylaniline in 170 ml ethanol was added 0.3 ml concentrated hydrochloric acid, and the mixture was hydrogenated at 35 psi pressure by using 5% Pd/C (100 mg) as a catalyst. The reaction mixture was filtered and evaporated in vacuo to give an oil. The oil was dissolved in 100 ml dry tetrahydrofurane and 1.3 ml (13.9 mmol) dry triethylamine was added. 1.6 ml (13.9 mmol) ethyl oxalylchloride was added dropwise, and the reaction mixture was stirred for 2 h. The reaction mixture was filtered and evaporated in vacuo to give an oil A mixture of the oil, 100 ml 1N hydrochloric acid and 50 ml ethanol was refluxed for 2 h. After cooling to 25° C. the precipitate was filtered off and stirred with 100 ml ether. The product was filtered off and dried to give 0.32 g (14%) 1-cyclohexyl-6- trifluoromethylquinoxaline-2,3(1H,4H)-dione. M.p. (DSC): decomp. $^1$H-NMR (DMSO-d$_6$): 13.5–10.5 (1H, broad s), 8.0–7.2 (3H, m), 4.6 (1H, m), 2.8–1.0 (10H, m). MS m/e: 312 (M+, 10%), 231 (100%).

EXAMPLE 20 a. N-Diphenylmethyl-2-amino-4-fluoroaniline

To a solution of 3.2 ml (19 mmol) diphenylaminomethan and 2.7 ml (19 mmol) triethylamine in 100 ml dimethylformamide was added 3.0 g (19 mmol) 2,5-difluoronitrobenzene. The reaction mixture was stirred at 80° C. for 4 h. After cooling to 25° C. the reaction mixture was evaporated in vacuo to give an oil. The oil, 100 ml water and 100 ml ether was shaken. The ether phase was dried with sodium sulphate, filtered and evaporated in vacuo. The crude product was washed with 20 ml dry ethanol to give 1.8 g (30%) N-Diphenylmethyl-2-amino-4-fluoroaniline. M.p. 119.5° C., $^1$H-NMR (CDCl$_3$): 8.5–6.4 (4H, m), 7.2 (10H, s), 5.7 (1H, d).

b.
1-Diphenylmethyl-6-fluoroquinoxaline-2,3(1H,4H)-dione (Compound 20)

A solution of 1.6 g (5.0 mmol) N-diphenylmethyl-2-amino-4-fluoroaniline in 100 ml ethyl acetate was hydrogenated at atm. pressure by using 5% Pd/C (100 mg) as a catalyst. The reaction mixture was filtered and 4.2 ml (30 mmol) dry triethylamine was added 3.4 ml (30 mmol) ethyl oxalylchloride was added dropwise, and the reaction mixture was stirred for 1 h. The reaction mixture was filtered and evaporated in vacuo to give an oil. A mixture of the oil, 40 ml 1N hydrochloric acid and 60 ml ethanol was stirred at 80° C. for 4 h. After cooling to 25° C. 50 ml H$_2$O was added, and the precipitate was filtered off. The crude product was dissolved in 20 ml ethanol, filtered and evaporated in vacuo to give an oil. The oil was stirred with 30 ml water for 1 h. The product was filtered off and dried to give 0.4 g (23%) 1-diphenylmethyl-6-fluoroquinoxaline-2,3(1H,4H)-dione. M.p. 143.8° C., $^1$H-NMR (CDCl$_3$): 8.5–6.5 (3H, m), 7.2 (10H, s) 3.8 (1H, m).

EXAMPLE 21

1-Carboxymethylquinoxaline-2,3(1H,4H)-dione (Compound 21)

To a solution of 3.0 g (15 mmol) 1,2,3,4-tetrahydro-3-oxoquinoxaline-1-acetic acid in 50 ml water was added gradually a solution of 4.0 g (25 mmol) potassium permanganate in aqueous sodium hydroxide (4%, w/v) and the mixture was refluxed for 4 h. The reaction mixture was cooled, filtered and the filtrate acidified with concentrated hydrochloric acid to pH 2.5. The precipitate was filtered off and washed with water to give 2.2 g (69%) 1-carboxymethylquinoxaline-2,3(1H,4H)- dione. M.p. >300° C. $^1$H-NMR (DMSO-d$_6$): 12.0 (1H, broad s), 7.2 (4H, s), 7.0–5.0 (1H, broad s), 4.9 (2H, s).

EXAMPLE 22

1-Methoxycarbonylmethylquinoxaline-2,3(1H,4H)-dione (Compound 22)

A mixture of 1.0 g (4.5 mmol) 1-carboxymethyl-quinoxaline-2,3(1H,4H)-dione, 15 ml dry methanol and 0.2 ml concentrated sulfuric acid was stirred at 80° C. for 1 h. After cooling to 25° C. the reaction mixture was poured in water and made alkaline. The precipitate was filtered off and recrystallized (acetone) to give 0.22 g (21%) 1-methoxycarbonylmethylquinoxaline-2,3(1H,4H)-dione. M.p. 269° C. $^1$H-NMR (DMSO-d$_6$): 12.0 (1H, broad s), 7.1 (4H, s), 4.9 (2H, s), 3.7 (3H, s).

EXAMPLE 23

1-Isopropoxycarbonylmethylquinoxaline-2,3(1H,4H)-dione (Compound 23)

A mixture of 1.0 g (4.5 mmol) 1-carboxymethyl-quinoxaline-2,3(1H 4H)-dione, 50 ml 2-propanol and 0.5 ml concentrated sulfuric acid was refluxed for 18 h. After cooling to 25° C. the reaction mixture was poured in water, and the precipitate was filtered off. The product was washed with water and dried to give 0.71 g (60%) 1-isopropoxycarbonyl-methylquinoxaline-2,3(1H,4H)-dione. M.p. 228° C., $^1$H-NMR (DMSO-d$_6$); 12.2 (1H, broad s), 7.1 (4H, s), 4.9 (3H, m), 1.2 (6H, d).

EXAMPLE 24

1-Carbamoylmethylquinoxaline-2,3(1H,4H)-dione (Compound 24)

A mixture of 0.17 g (0.7 mmol) 1-methoxycarbonyl-methylquinoxaline-2,3(1H,4H)-dione and 10 ml 25% aqueous ammonia was stirred for 18 h. The product was filtered off and washed with cold water to give 0.05 g (32%) 1-carbamoylmethylquinoxaline-2,3(1H,4H)- dione. M.p. >300° C. MS m/c: 219 (M+, 40%), 119 (100%).

EXAMPLE 25 a. N-Carboxyethyl-2-nitroaniline

A mixture of 5.0 g (36 mmol) 2-fluoronitrobenzen, 6.3 g (71 mmol) β-alanin, 20 ml triethylamine, 50 ml water and 100 ml dimethylformamide was stirred at 80° C. for 10 h After cooling to 25° C. the reaction mixture was evaporated in vacuo. The residue was stirred with 1N hydrochloric acid, and the precipitate was filtered off and washed with water to give 3.6 g (48%) N- carboxyethyl-2-nitroaniline. M.p. 145° C., $^1$H-NMR (DMSO-$d_6$): 8.2–6.2 (5H, m), 3.4 (2H, q), 2.5 (2H, t).

b. 1-Carboxyethylquinoxaline-2,3(1H,4H)-dione (Compound 25)

1.5 g (7.1 mmol) N-carboxyethyl-2-nitroaniline was dissolved in 50 ml ethanol and the solution was hydroqenated at atm. pressure by using 5% Pd/C (100 mg) as a catalyst. The reaction mixture was filtered and evaporated. 50 ml 4N hydrochloric acid and 1.6 g (13 mmol) oxalic acid dihydrate was added, and the reaction mixture was refluxed for 2 h. After cooling to 25° C. the precipitate was filtered off, washed with water and ethanol to give 0.4 g (24%) 1-carboxyethylquinoxaline-2,3(1H,4H)-dione. M.p. >300° C. $^1$H-NMR (DMSO-$d_6$): 12.0 (1H, broad s), 7.2 (4H, m), 4.3 (2H, t), 2.6 (2H, t).

EXAMPLE 26 a. N-(2-Hydroxy-1-methyl)ethyl-2-nitroaniline

A mixture of 3.8 ml (36 mmol) 2-fluoronitrobenzen, 6.0 g (80 mmol) alaninol, 10 ml triethylamine and 100 ml dimethylformamide was stirred at 80° C. for 2½ h. After cooling to 25° C. the reaction mixture was evaporated in vacuo. The residue in 50 ml ethyl acetate was washed with water (2×30 ml). The ethyl acetate phase was dried and evaporated in vacuo. The residue was stirred with 50 ml pentane, and the precipitate was filtered off to give 5.3 g (75%) N-(2-hydroxy-1-methyl)ethyl-2-nitroaniline. M.p. 70.8° C.

b. 1-((2-Hydroxy-1-methyl)ethyl)quinoxaline-2,3(1H,4H)-dione (Compound 26)

5.0 g (26 mmol) N-(2-hydroxy-1-methyl)ethyl-2-nitroaniline was dissolved in 100 ml ethanol and the solution was hydrogenated at atm. pressure by using 5% Pd/C (200 mg) as a catalyst. The reaction mixture was filtered and evaporated. The residue, 8.0 g (63 mmol) oxalic acid dihydrate and 200 ml 4N hydrochloric acid was refluxed for 1 h. After cooling to 25° C. the precipitate was filtered off and washed with water to give 2.2 g (39%) 1-((2-hydroxy-1-methyl)ethyl)quinoxaline-2,3(1H,4H)-dione. M.p. 241.2° C. $^1$H-NMR (DMSO-$d_6$): 12.0 (1H, broad s), 7.8–6.9 (4H, m), 5.2–3.2 (4H, m), 1.5 (3H, d).

EXAMPLE 27 a. 4-X-benzo[f]quinoxaline-2,3(1H,4H)-diones

To a solution of 6-bromo-2-methoxy-1-nitronaphthalene (5.64 g, 20 mmol) in 100 ml of dry N,N-dimethylformamide was added an excess (50–100 mmol) of the X-NH$_2$ and the mixture was stirred at 80° C. on an oil bath until the methoxynaphthalene had disappeared according to thin layer chromatography (4–20 h). Then the mixture was evaporated to dryness under reduced pressure and the residue was triturated with light petroleum or ether to give the N-X-6-bromo-1-nitro-2-naphthylamine. A suspension of the crude nitronaphthalene in 100 ml of 96% ethanol was hydrogenated at room temperature and atmospheric pressure in the presence of 5% palladium on carbon (100–500 mg) until the theoretical amount of hydrogen was absorbed. The catalyst was filtered off under a nitrogen atmosphere and the filtrate was evaporated to dryness to give the crude N$^2$-X-1.2-naphthalenediamino monohydrobromide. The hydrobromide was triturated with ether or used in the next step without purification. The 1,2-naphthalenediamine hydrobromide was dissolved or suspended in 100 ml of dry tetrahydrofuran and two equivalents of dry triethylamine were added with stirring at 0° C.. Then a solution of one equivalent of ethyl oxalylchloride in 20 ml of dry tetrahydrofuran was added dropwise with stirring in an ice bath. The reaction mixture was stirred at 0° C. for 1–2 h, then it was heated to reflux for 2–5 h in order to complete the cyclization of the intermediate ethoxalYlaminonaphthalene. After cooling to 0° C., the precipitate Was isolated by filtration and washed successively with tetrahydrofuran, water, ethanol and ether to give the 4-X-benzo[f]quinoxaline. If necessary, the crude product was recrystallized from a suitable solvent. Yields given are overall yields from 6-bromo-2-methoxy-1-nitronaphthalene to the benzo[f]quinoxaline.

b. 4-Butylbenzo[f]quinoxaline-2,3(1H,4H)-dione (Compound 27b)

Yield 45%; m.p. 268.8° C. (DSC); IR (KBr): 1680 cm$^{-1}$; $^1$H-NMR (DMSO-$d_6$): 0.77–1.93 (m, 7H, CH$_2$CH$_2$CH$_3$), 4.03–4.40 (m, 2H, NCH$_2$), 7.40–8.03 (m, 5H, ArH), 8.43–8.73 (m, 1H, ArH), 12.2 (broad s, 1H, NH); MS (m/z): 268 (M+, 84%).

c. 4-Hexylbenzo[f]quinoxaline-2,3(1H,4H)-dione (Compound 27c)

Yield 16%; m.p. 195.8–196.4° C. (ethanol/water); IR (KBr): 1690 cm$^{-1}$; $^1$H-NMR (CDCl$_3$): 0.73–2.00 (m, 11H, (CH$_2$)$_4$CH$_3$), 3.93–4.30 (m, 2H, NCH$_2$), 6.93–8.47 (m, 6H, ArH); 11.5 (broad s, 1H, NH); MS (m/z): 296 (M+, 100%).

d. 4-Dodecylbenzo[f]quinoxaline-2,3(1H,4H)-dione (Compound 27d)

Yield 15%; m.p. 180.4–180.5° C. (ethyl acetate); IR (KBr): 1710, 1665 and 1655 cm$^{-1}$; $^1$H-NMR (CDCl$_3$): 0.73–1.90 (m, 23H, (CH$_2$)$_{10}$CH$_3$), 3.97–4.33 (m, 2H, NCH$_2$), 7.10–8.67 (m, 6H, ArH), 11.6 (broad s, 1H, NH); MS (m/z): 380 (M+, 25%).

e. 4-Cyclopropylmethylbenzo[f]quinoxaline-2,3(1H,4H)-dione (Compound 27e)

Yield 64%; m.p. 292.4° C. (DSC); IR (KBr): 1700 cm$^{-1}$; $^1$H-NMR (DMSO-$d_6$): 0.50 (d, J=6 Hz, 4H, CH$_2$CH$_2$), 1.03–1.53 (m, 1H, CH), 4.20 (d, J=6 Hz, 2H, NCH$_2$); 7.33–8.77 (m, 6H, ArH), 12.2 (broad s, 1H, NH); MS (m/z): 266 (M+, 71%).

f. 4-Benzylbenzo[f]quinoxaline-2,3(1H,4H)-dione (Compound 27f)

Yield 10%; m.p. 308.4° C. (DSC); IR (KBr): 1685 cm$^{-1}$; $^1$H-NMR (DMSO-$d_6$): 5.53 (s, 2H, CH$_2$), 7.23–8.80 (m, 11H, ArH), 12.2 (broad s, 1H, NH); MS (m/z): 302 (M+, 100%).

g. 4-(3,3-Pentamethylenebutyl)benzo[f]quinoxaline-2,3(1H,2H)-dione (Compound 27g)

Yield 23%; m.p. 265.6° C. (DSC); IR (KBr): 1680 cm$^{-1}$ ; $^1$H-NMR (DMSO-d$_6$): 1.05 (s, 3H, CH$_3$), 1.20–1.83 (m, 12H, 6×CH$_2$), 3.97–4.33 (m, 2H, NCH$_2$), 7.25–8.63 (m, 6H, ArH), 12.2 (broad s, 1H, NH); MS (m/z): 336 (M+, 20%).

h. 4-Cyclopropylbenzo[f]quinoxaline-2,3(1H,4H)-dione (Compound 27h)

The general procedure was followed except that the suspension of the intermediate 1-amino-2-cyclopropylaminonaphthalene hydrobromide in 100 ml of dry tetrahydrofuran was treated with three equivalents of dry triethylamine followed by the dropwise addition of two equivalents of ethyl oxalylchloride in 10 ml of dry tetrahydrofuran at 0° C. Then the mixture was stirred at room temperature over night and filtered. The filtrate was evaporated to dryness and the residue was heated to reflux in 50 ml of 4M hydrochloric acid for 15 h. After cooling the crude product was isolated by filtration. Recrystallization from N,N-dimethylformamide afforded the pure title compound in 50% yield; m.p. 306.9° C. (DSC); IR (KBr): 1680 cm$^{-1}$; $^1$H-NMR (DMSO-d$_6$): 0.57–1.53 (m, 4H, CH$_2$CH$_2$), 2.90–3.27 (m, 1H, CH), 7.40–8.73 (m, 6H, ArH), 12.0 (broad s, 1H, NH); MS (m/z): 252 (M+, 20%).

4-(2-Piperidinoethyl)benzo[f]quinoxaline-2,3(1H,4H)-dione (Compound 27i)

The modification of the general procedure described above was followed, except that the resulting diethoxalylamino compound was ring closed by heating to reflux in 40 ml of 4M hydrochloric acid for 3 h. The mixture was cooled and filtered to give 9% of the title compound as the hydrochloride; m.p. >300° C.; IR (KBr): 2600–2300, 1680 cm$^{-1}$; MS (m/z): 323 (M+, 2%).

j. 4-Cyclopentylbenzo[f]quinoxaline-2,3(1H,4H)-dione (Compound 27j)

The modification of the general procedure described above was followed, except that ring closure was carried out by heating to reflux in 50 ml of 4M hydrochloric acid for 4 h. After cooling, the precipitate was isolated by filtration and washed with water and ethanol Recrystallization from N,N-dimethylformamide/water with decolourising carbon afforded 1.5 g (27%) of the pure title compound; m.p. 294.0° C. DSC); IR (KBr): 1680 cm$^{-1}$; $^1$H-NMR (DMSO-d$_6$): 1.50–2.50 (m, 8H, 4 CH$_2$), 4.97–5.47 (m, 1H, NCH), 7.37–8.70 (m, 6H, ArH), 12.1 (broad s, 1H, NH); MS (m/z): 280 (M+, 29%).

k. 4-Cyclohexylbenzo[f]quinoxaline-2,3(1H,4H)-dione (Compound 27k)

The general procedure was followed starting from 42.2 g (0.16 mol) of 6-bromo-2-methoxy-1-nitronaphthalene to afford 24.6 g (52%) of the title compound; m.p. 288.3° C. (N,N-dimethylformamide; DSC); IR (KBr): 1680 cm$^{-1}$; $^1$H-NMR (DMSO-d$_6$): 1.17–2.93 (m, 10H, 5CH$_2$), 4.37–4.92 (m, 1H, NCH), 7.33–8.78 (m, 6H, ArH), 12.0 (broad s, 1H, NH); MS(m/z): 294 (M+, 21%).

l. 4-(exo-2-Norbornyl)benzo[f]quinoxaline-2,3(1H,4H)-dione (Compound 27l)

The modified procedure for the preparation of 4-cyclopentylbenzo[f]quinoxaline-2,3(1H,4H)-dione was followed to give 21% of the pure title compound; m.p. 308.6° C. (N,N-dimethylformamide; DSC); IR (KBr): 1690 cm$^{-1}$; $^1$H-NMR (DMSO-d$_6$): 1.15–2.97 (m, 10H, 4CH$_2$+2); 4.09–4.43 (m, 1H, NCH), 7.53–8.83 (m, 6H, ArH), 11.8 (broad s, 1H, NH); MS (m/z): 306 (M+, 17%).

EXAMPLE 28 a. N-(2-hydroxyethyl)-4-chloro-2-nitroaniline

To a solution of 10 g (52 mmol) 2,5-dichloronitrobenzene in 40 ml butanol was added 6.5 g (104 mmol) ethanolamine, and the mixture was refluxed for 20 h. The reaction mixture was evaporated in vacuo. The residue was recrystallized (toluene) to give 8.1 g (75%) N-(2-hydroxyethyl)-4-chloro-2-nitroaniline. M.p. 98°–100° C.

b. 6-Chloro-1-(2-hydroxyethyl)-quinoxaline-2,3(1H,4H)-dione (Compound 28)

A solution of 1.0 g (4.6 mmol) N-(2-hydroxyethyl)-4-chloro-2-nitroaniline in 100 ml ethanol was hydrogenated at atm. pressure by using Ra-Ni (1 g) as a catalyst. The reaction mixture was filtered and evaporated in vacuo. The residue was added 100 ml 4N hydrochloric acid and 1.4 g oxalic acid dihydrate, and the mixture was refluxed for 3 h. After cooling to 25° C., the precipitate was filtered off and washed with water. The crude product was recrystallized (dimethylformamide-water) to give 0.55 g (50%) of 6-chloro-1-(2-hydroxyethyl)-quinoxaline-2,3(1H,4H)-dione. M.p. 295° C. $^1$H-NMR (DMSO-d$_6$): 12.0 (1H, broad s), 7.6–7.0 (3H, m), 4.8 (1H, broad s), 4.1 (2H, t), 3.6 (2H, m). MS (m/e): 240 (M+, 40%).

EXAMPLE 29 a. 4-Chloro-2-ethoxalylamine-1-nitrobenzene

A solution of 10 g (58 mmol) 5-chloro-2-nitroaniline in 250 ml dry tetrahydrofuran was added 8.5 ml (62 mmol). dry triethylamine. A solution of 7.0 ml (62.7 mmol) ethoxalylchloride in 50 ml dry tetrahydrofuran was added dropwise Stirring was continued at 25° C. for 20 h. The reaction mixture was filtered and evaporated in vacuo. The residue was stirred with ethanol to give 9.0 g (57%) 4-chloro-2-ethoxalylamino-1-nitrobenzene. M.p. 105.1° C.

b. 6-Chloro-1-hydroxyquinoxaline-2,3(1H,4H)-dione (Compound 29)

A solution of 2 g (7.3 mmol) 4-chloro-2-ethoxalylamino-1-nitrobenzene in 50 ml dimethylformamide was hydrogenated at atm. pressure by using Ra-Ni (0.2 g) as a catalyst. The reaction mixture was filtered and evaporated in vacuo. The residue was stirred with water to give a crude product. Recrystallization (dimethylformamide-water) gave 1.2 g (78%) 6-chloro-1-hydroxyquinoxaline-2,3(1H,4H)-dione. M.p. >300° C. M.p. >300° C. $^1$H-NMR (DMSO-d$_6$): 11.8 (2H, broad s), 7.2 (3H, m). MS (m/e): 212 (M+, 60%).

EXAMPLE 30

1-Acetoxy-6-chloroquinoxaline-2,3(1H,4H)-dione (Compound 30)

A solution of 0.4 g (1.9 mmol) 6-chloro-1-hydroxyquinoxaline-2,3(1H,4H)-dione in 15 ml 0.5N sodium hydroxide was added with stirring 1 ml acetic anhydride. Stirring was continued at 25° C. for 1 h to give a precipitate. Recrystallization (dimethylformamide-water) gave 0.2 g (42%) 1-acetoxy-6-chloroquinoxaline-2,3(1H,4H)-dione. M.p. 219° C. $^1$H-NMR (DMSO-$d_6$): 12.5 (1H, broad s), 7.2 (3H, m), 2.50 (3H, s). MS (m/e). 254 ($M^+$, 30%).

EXAMPLE 31

1-Cyanomethylquinoxaline-2,3(1H,4H)-dione (Compound 31)

A solution of ethyl oxalylchloride (2.1 ml, 20 mmol) in 10 ml of dry tetrahydrofuran was added dropwise to a stirred solution of N-cyanomethyl-1,2-phenylenediamine (3.0 g, 20 mmol) and dry triethylamine (2.80 ml, 20 mmol) in 70 ml of dry tetrahydrofuran at 0° C.. After 20 min. the ice-bath was removed and the mixture was stirred at room temperature for 1½ h. The mixture was filtered, and the filtrate was heated at reflux for 3 h. The mixture was allowed to cool and a solid was isolated by filtration and washed with ether to give 3.53 g (88%) of the pure title compound. M.p. 339.5° C. (DSC); IR (KBr): 2240, 1680 cm$^{-1}$; $^1$H-NMR (DMSO-$d_6$): 5.28 (s, 2H, CH$_2$), 7.07–7.57 (m, 4H, ArH), 12.1 (broad s, 1H, NH); MS (m/z): 201 ($M^+$, 66%).

EXAMPLE 32

1-(5-Tetrazolyl)methylquinoxaline-2,3(1H,4H)-dione (Compound 32)

To a solution of 1-cyanomethylquinoxaline-2,3(1H,4H)-dione (0.60 g, 3.0 mmol) in 10 ml of N,N-dimethylformamide was added ammonium chloride (0.18 g, 3.4 mmol) and sodium azide (0.22 g, 3.4 mmol), and the mixture was stirred on an o±I bath at 100° C. for 4 h. The mixture was cooled to room temperature and 25 ml of 1M hydrochloric acid was added. The precipitated solid was isolated by filtration and washed with water, ethanol and ether to give 0.71 g (97%) of the title compound. M.p. 320.4° C. (DSC); IR (KBr): 1700, 1650, 1600 cm$^{-1}$; $^1$H-NMR (DMSO-$d_6$): 5.62 (s, 2H, CH$_2$), 7.08 (s, 4H, ArH), 12.2 (broad s, 1H, NH; only one exchangeable proton could be seen); MS (m/z): 244 ($M^+$, 49%).

EXAMPLE 33

6-Cyano-1-cyclohexylbenzo[f]quinoxaline-2,3(1H,4H)-dione (Compound 33)

A solution of 100% nitric acid (0.91 ml, 22 mmol) in 8 ml of acetic anhydride was added dropwise to a solution of 1-cyano-4-methoxynaphthalene (3.66 g, 20 mmol) in 50 ml of acetic anhydride containing two drops of conc. sulfuric acid while maintaining the temperature at −30° to −40° C. The mixture was stirred for an additional 10 min. and filtered. The solid was washed with water and dried to give 3.5 g (77%) of 4-cyano-1-methoxy-2-nitronaphthalene. The crude product was dissolved in a mixture of 25 ml of tetrahydrofuran and 10 ml of N,N-dimethylformamide. Then 5 ml of cyclohexylamine was added, and the mixture was stirred at room temperature for 2 h. The mixture was evaporated to dryness, and the residue was triturated with light petroleum to give 4.5 g (90%) of 4-cyano-1-cyclohexylamino-2-nitronaphthalene. The crude product, suspended in 200 ml of 96% ethanol, was hydrogenated at room temperature and atmospheric pressure in the presence of 5% palladium-on-carbon. When the theoretical amound of hydrogen was taken up, the catalyst was filtered off, and the filtrate was evaporated to dryness. The resulting diaminonaphthalene was immediately suspended in a mixture of 20 ml of dry tetrahydrofuran and dry triethylamine (1.95 ml, 14 mmol). Then a solution of ethyl oxalylchloride (1.56 ml, 14 mmol) in 10 ml of dry tetrahydrofuran was added dropwise with stirring at 0° C. The mixture was stirred at room temperature over night, and then heated at reflux for 1 h. The cooled mixture was filtered, and the solid was washed with tetrahydrofuran and water. Recrystallization from 2-methoxyethanol afforded 1.84 g (41%) of the title compound. M.p. >300° C.; IR (KBr): 2220, 1700 cm$^{-1}$; $^1$H-NMR (DMSO-$d_6$): 0.93–4.77 (m, 11H, cyclohexyl), 7.97–8.63 (m, 5H, ArH), 11.8 (broad s, 1H, NH); MS (m/z): 319 ($M^+$, 16%).

Anal. Calcd. for $C_{19}H_{17}N_3O_2$: C 71.46; H 5.37; N 13.16. Found C 70.73; H 5.35; N 13.02

EXAMPLE 34

1-(2-Phenylethyl)benzo[f]quinoxaline-2,3(1H,4H)-dione (Compound 34)

A solution of 4-bromo-1-methoxy-2-nitronaphthalene (2.82 g, 10 mmol) and 2-phenylethylamine (1.4 ml, 11 mmol) in 20 ml of dry N,N-dimethylformamide was stirred at 80° C. for 2 h, and evaporated to dryness in vacuo. The crude 4-bromo-2-nitro-1-phenylethylaminonaphthalene (3.7 g, 10 mmol) was suspended in 100 ml of 96% ethanol. Dry triethylamine (1.4 ml, 10 mmol) was added, and the mixture was hydrogenated at room temperature and atmospheric pressure in the presence of 5% palladium-on-carbon (300 mg) for 6 h. The catalyst was filtered off, and the filtrate was evaporated to dryness. The residue was taken up in 25 ml of dry tetrahydrofuran, and dry triethylamine (1.4 ml, 10 mmol) was added. Then a solution of ethyl oxalylchloride (1.2 ml, 10 mmol) in 5 ml of dry tetrahydrofuran was added dropwise with stirring at 0° C. The mixture was stirred over night at room temperature and evaporated to dryness. The residue was triturated with 40 ml of ethanol and filtered. Washing with water and ethanol afforded 0.70 g (22%) of the title compound. M.p. 268.1° C. (DSC); IR (KBr): 1680 cm$^{-1}$; $^1$H-NMR (DMSO-$d_6$): 3.03 (distorted t,J=7 Hz, 2H, CH$_2$), 4.56 (distorted t,J=7 Hz, 2H, NCH$_2$), 6.80–8.20 (m, 11H, ArH), 11.8 (broad s, 1H, NH); MS (m/z): 316 ($M^+$, 60%).

EXAMPLE 35

6-Bromo-1-methylbenzo[f]quinoxaline-2,3(1H,4H)-dione (Compound 35)

A suspension of 4-bromo-1-methylamino-2-nitronaphthalene (1.12 g, 4 mmol) in 60 ml of 96% ethanol was hydrogenated at room temperature and atmospheric pressure in the presence of Ni/Raney After the hydrogen uptake was completed, the reaction mixture was filtered and 25 ml of 4M hydrochloric acid was added to the filtrate. Concentration to dryness afforded 1.1 g (92%) of crude 2-amino-4-bromo-1-methylaminonaphthalene hydrochloride. To a suspension of the hydrochloride and dry triethylamine (1.06 ml, 7.6 mmol) in 75 ml of dry tetrahydrofuran was added a solution of ethyl oxalylchloride (0.42 ml, 3.8 mmol) in 15 ml of dry tetrahydrofuran dropwise with stirring at 0° C.. Then the mixture was stirred at room tempeature for 2 h, and filtered. The filtrate was evaporated to dryness, and the residue was heated at reflux in 40 ml of 4M hydrochloric acid for 2 h. After cooling, the precipitate was isolated by filtration and washed with water and ethanol. Recrystallization from ethanol/N,N-dimethylformamide afforded 0.39 g (34%) of the pure title compound. M.p. 315.0° C. (DSC); IR (KBr): 1690 cm$^{-1}$; $^1$H-NMR (DMSO-d$_6$): 3.70 (s, 3H, CH$_3$), 7.33–8.33 (m, 5H, ArH), 12.1 (broad s, 1H, NH); MS (m/z): 304 (M$^+$, 100%).

EXAMPLE 36

6-Bromo-1-cyclohexylbenzo[f]quinoxaline-2,3(1H,4H)-dione (Compound 36)

A solution of 4-bromo-1-methoxy-2-nitronaphthalene (10.0 g, 35.5 mmol) and 12.5 ml of cyclohexylamine in 40 ml of dry tetrahydrofuran was stirred at room temperature for 1 h. The mixture was evaporated to dryness. Crude 4-bromo-1-cyclohexylamino-2-nitronaphthalene (12.1 g, 98%) was suspended in 350 ml of 96% ethanol and hydrogenated at room temperature and atmospheric pressure over Ni/Raney After the hydrogen uptake was completed, the reaction mixture was filtered into 150 ml of 4M hydrochloric acid and concentrated to dryness. Crude 2-amino-4-bromo-1-cyclohexylaminonaphthalene hydrochloride (11.7 g, 95%) was taken up in 80 ml of dry tetrahydrofuran followed by addition of dry triethylamine (9.2 ml, 66 mmol). A solution of ethyl oxalylchloride (3.7 ml, 33 mmol) in 20 ml of dry tetrahydrofuran was added dropwise with stirring at 0° C.. Then the mixture was stirred at room temperature for 4 h and at reflux for 3 h After cooling, the solid was isolated by filtration and washed successively with tetrahydrofuran, water and ethanol to give 3.0 g (24%) of pure title compound M.p. 340.6° C. (DSC); IR (KBr): 1690 cm$^{-1}$; $^1$H-NMR (DMSO-d$_6$): 1.23–4.77 (m, 11H, cyclohexyl), 7.13–8.23 (m, 5H, ArH), 11.9 (broad s, 1H, NH); MS m/z): 372 (M$^+$, 14%).

EXAMPLE 37

8-Bromo-4-cyclohexylbenzo[f]quinoxaline-2,3(1H,4H)-dione (Compound 37)

A solution of 6-bromo-2-methoxy-1-nitronaphthalene (10.0 g, 35.6 mmol) and 8 ml of cyclohexylamine in 50 ml of dry N,N-dimethylformamide was heated with stirring at 120° C. for 17 h. The mixture was evaporated to dryness and the residue was triturated with 50 ml of ethanol at 0° C.. The solid was isolated by filtration and washed with light petroleum to give 10.4 g (84%) of 6-bromo-2-cyclohexylamino-1-nitronaphthalene. The crude product was suspended in 150 ml of 96% ethanol and hydrogenated at room temperature and 40 psi over Ni/Raney After the hydrogen uptake was completed, the reaction mixture was filtered into 50 ml of 4M hydrochloric acid and concentrated to dryness. Crude 1-amino-6-bromo-2-cyclohexylaminonaphthalene hydrochloride (9.8 g, 27.6 mmol) was taken up in 80 ml of dry tetrahydrofuran. Dry triethylamine (7.7 ml, 55.3 mmol) was added, followed by the dropwise addition of ethyloxalyl chloride (3.1 ml, 27.7 mmol) with stirring at 0° C.. The mixture was stirred over night at room temperature and finally at reflux for 4 h. The cooled mixture was filtered and the solid was washed with water and ethanol affording 5.2 g (51%) of the title compound M.p. 347.0° C. (N,N-dimethylformamide, DSC); IR (KBr): 1700 cm$^{-1}$; $^1$H-NMR (DMSO-d$_6$): 1.13–2.93 (m, 10H, 5CH$_2$), 4.33–4.90 (m, 1H, NCH), 7.47–8.67 (m, 5H, ArH), 12.1 (broad s, 1H, NH); MS (m/z): 372 (M$^+$, 17%).

EXAMPLE 38

1-Methylbenzo[f]quinoxaline-2,3(1H,4H)-dione (Compound 38)

A suspension of 4-bromo-1-methylamino-2-nitronaphthalene (1.69 g, 6 mmol) and triethylamine (0.84 ml, 6 mmol) in 100 ml of 96% ethanol was hydrogenated at room temperature and atm. pressure in the presence of 5% palladium-on-carbon (300 mg) for 90 min. The catalyst was filtered off under a nirrogen atmosphere, and the filtrate was evaporated to dryness. The residue was triturated with 50 ml of dry ether, and triethylamine hydrochloride was filtered off and washed with 25 ml of dry ether. The combined filtrate was evaporated to give 0.80 g (77%) of the crude diamino compound as a dark oil. Without purification the oil was refluxed with oxalic acid dihydrate (0.76 g, 6 mmol) in 15 ml of 4M hydrochloric acid for 2 h. The mixture was allowed to cool to room temperature, and the precipitated product was collected by filtration and washed with water, ethanol and ether to afford 0.52 g (52%) of the title compound M.p. 294°–295° C.; IR (KBr): 1665 cm$^{-1}$; $^1$H-NMR (DMSO-d$_6$): 3.78 (s, 3H, CH$_3$), 7.16–8.33 (m, 6H, ArH), 12.12 (broad s, 1H, NH; MS m/z: 226 (M$^+$, 100%).

EXAMPLE 39

1-Methyl-6,7-dinitrobenzo[f]quinoxaline-2,3(1H,4H)-dione (Compound 39)

Finely powdered potassium nitrate (0.20 g, 2 mmol) was added to a stirred solution of 1-methylbenzo[f]quinoxaline-2,3-(1H,4H)-dione (0.23 g, 1 mmol) in 5 ml of conc. sulfuric acid at 0° C.. The mixture was stirred over night at room temperature and poured into 50 ml of ice/water. The yellow precipitate was isolated by filtration, washed with water and recrystallized once from acetic acid and once from N,N-dimethylformamide/water affording 0.13 g (41%) of the title compound slightly contaminated with another dinitro compound M.p >300° C. decomp.; IR (KBr): 1710, 1535 and 1350 cm$^{-1}$; $^1$H-NMR (DMSO-d$_6$): 3.77 (s, 3H, CH$_3$), 7.63–8.86 (m, 4H, ArH), (broad s, 1H, NH); MS (m/z): 316 (M$^+$, 100%).

EXAMPLE 40

4-Methyl-6,7-dinitrobenzo[f]quinoxaline-2,3(1H,4H)-dione (Compound 40)

Finely powdered potassium nitrate (0.41 g, 4 mmol) was added to a stirred solution of 4-methylbenzo[f]quinoxaline-2,3(1H,4H)-dione (0.45 g, 2 mmol) in 10 ml of conc. sulfuric acid at 0° C.. After stirring at 0° C. for 30 min. the mixture was poured into 50 ml of ice/water. A yellow solid was isolated by filtration and washed with water and a small amount of ethanol and ether. The crude product was recrystallized from acetic acid affording 0.20 g (32%) of the title compound, which contained trace amounts of another dinitroisomer. M.p. >325° C. decomp.; IR (KBr): 1690, 1540 and 1350 cm$^{-1}$; $^1$H-NMR (DMSO-d$_6$): 3.68 (s, 3H, CH$_3$), 7.67-9.13 (m, 4H, ArH), 12.5 (broad s, 1H, NH); MS (m/z): 316 (M+, 32%).

In conclusion, from the foregoing, it is apparent that the present invention provides novel neurologically-effective quisqualate antagonist quinoxaline compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

We claim:

1. A quinoxaline compound having the formula I

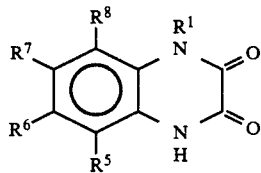

wherein
$R^1$ is $C_{1-12}$-alkyl, which may optionally be substituted by hydroxy, formyl, carboxy, carlomoyl, piperedino, amino, $C_{3-8}$-cycloalkyl, or phenyl; or R is $C_{3-6}$ cycloalkyl and in any case
$R^5$ and $R^6$ together form a further fused benzene ring, which may be substituted with halogen, $NO_2$, CN, $CF_3$ or OR', wherein R' is $C_{1-4}$-alkyl, and $R^7$ and $R^8$ independently are hydrogen, halogen, CN, $CF_3$, $NO_2$ or OR', wherein R' is $C_{1-4}$-alkyl; or
$R^7$ and $R^8$ together form a further fused benzene ring, which may be substituted with halogen, $NO_2$, CN, $CF_3$ or OR', wherein R' is $C_{1-4}$-alkyl, and $R^5$ and $R^6$ independently are hydrogen, halogen, CN, $CF_3$, $NO_2$ or OR', wherein R' is $C_{1-4}$-alkyl.

2. A compound of claim 1, which is 4-methylbenzo[f]quinoxaline-2,3(1H,4H)-dione.

3. A compound of claim 1, which is 4-butylbenzo[f]quinoxaline-2,3(1H,4H)-dione.

4. A compound of claim 1, which is 4-(2-piperidino-ethyl) benzo[f]quinoxaline-2,3(1H,4H)-dione.

5. A compound of claim 1, which is 4-cyclohexylbenzo[f]-quinoxaline-2,3(1H,4H)-dione.

6. A compound of claim 1, which is 1-methyl-6,7-dinitrobenzo[f]-quinoxaline-2,3(1H,4H-dione.

7. A pharmaceutical composition useful as a neuroleptic comprising as active component a neuroleptically effective amount of a quinoxaline compound according to claim 1 or a pharmaceutically acceptable salt thereof and a pharmaceutically acceptable carrier.

8. A pharmaceutical composition according to claim 7 in the form of an oral dosage unit containing about 50-200 mg of the active compound.

9. A method of treating hyperactivity of the excitatory neurotransmitters in a subject in need thereof, which comprises the step of administering to the said subject a neuroleptically-effective amount of a compound of claim 1 or a pharmaceutically-acceptable salt thereof.

10. A method according to claim 9 wherein the compound is administered in the form of an oral dosage unit containing about 50 to 200 mg of the compound.

11. A method of claim 9, wherein the compound is administered in the form of a pharmaceutical composition containing the same together with a pharmaceutically-acceptable carrier.

12. A method of claim 9, wherein the neurotransmitters treated are the quisqualate receptors and the amount of the compound administered is a quisqualate-antagonistic amount of the compound.

* * * * *

UNITED STATES PATENT AND TRADEMARK OFFICE
CERTIFICATE OF CORRECTION

PATENT NO. : 5,026,704  
DATED : Jun 25, 1991  
INVENTOR(S) : Tage Honore, Poul Jacobsen, Flemming E. Nielsen, Lars Naerum It is certified that error appears in the above-identified patent and that said Letters Patent is hereby corrected as shown below:

Title Page, column 2, line 1; "F. Bernhardt" should read -- E. Bernhardt --.
Column 1, line 5; "4,948,749" should read -- 4,948,794 --. (R&A 12-12-90, P. 1 and orig Patent)
Column 1, line 8; "Of" should read -- of --.
Column 1, line 21; "diseases   Thus," should read -- diseases.  Thus, --.
Column 2, line 33; "receptor Certain" should read -- receptor. Certain --.
Column 2, line 41; "essense," should read -- essence, --.
Column 3, approximately line 17; "obtionally" should read -- optionally --.
Column 4, line 11; "$R^5, R^7$" should read -- $R^5, R^6, R^7$ --.
Column 5, line 2; "proliferation For" should read -- proliferation. For --.
Column 5, approximately line 52; "factors such" should read -- factors, such --.

Column 5, approximately line 62; "fattY" should read -- fatty --.
Column 6, line 20; "day. e.g.  about" should read -- day, e.g., about --.
Column 6, line 68; "neuroleptic especially" should read -- neuroleptic, especially --.
Column 8, approximately line 53; "precipitate" should read -- precipitate. --
Column 8, approximately line 57; "(1H,s),3.90" should read -- (1H,s), 6.87 (1H,s), 3.90 --.
Column 11, approximately line 20; "gradaully" should read -- gradually --.
Column 12, approximately line 44; "-2methoxy-" should read -- -2-methoxy- --.
Column 12, line 64; "palladiumon-" should read -- palladium-on- --.
Column 13, line 2; "withoutfurther" should read -- without further --.

UNITED STATES PATENT AND TRADEMARK OFFICE
CERTIFICATE OF CORRECTION

PATENT NO. : 5,026,704

DATED : Jun 25, 1991

INVENTOR(S) : Tage Honore, Poul Jacobsen, Flemming E. Nielsen, Lars Naerum

It is certified that error appears in the above-identified patent and that said Letters Patent is hereby corrected as shown below:

Column 13, approximately line 10/11; move the bracket "]" at the beginning of line 12 to the end of line 11 before the hyphen "-".
Column 13, line 68; "broad,s)" should read -- broad s) --.
Column 16, line 2; "added 3.4" should read -- added. 3.4 --.
Column 16, approximately line 51; "(1H4H)" should read --(1H,4H) --.
Column 17, line 1; "M+," should read -- $M^+$, --.
Column 17, approximately line 9; "h After" should read -- h. After --.
Column 18, approximately line 23; "ethoxalYlaminonaphthalene." should read -- ethoxalylaminonaphthalene. --.
Column 18, approximately line 24; "Was" should read -- was --.
Column 19, approximately line 34; "4-" should read -- i. 4- --.
Column 19, line 54; "DSC)" should read -- (DSC) --.
Column 21, line 41; "o+I" should read -- oil --.
Column 22, line 6; "amound" should read -- amount --.
Column 22, line 62; "Raney After" should read -- Raney. After --.
Column 23, line 36; "3 h After" should read -- 3 h. After --
Column 24, line 1; "compound" should read -- compound. --.

UNITED STATES PATENT AND TRADEMARK OFFICE
CERTIFICATE OF CORRECTION

PATENT NO. : 5,026,704

DATED : Jun. 25, 1991

INVENTOR(S) : Tage Honore, Poul Jacobsen, Flemming E. Nielsen, Lars Naerum

It is certified that error appears in the above-identified patent and that said Letters Patent is hereby corrected as shown below:

Column 24, line 50; after "ArH)," insert -- 12.3 --.

Column 25, line 31; "carlomoyl," should read -- carbamoyl, --.

Column 25, line 32; "piperedino," should read -- piperidino, --.

Column 25, line 33; "R" should read -- $R^1$ --.

Signed and Sealed this

Thirteenth Day of October, 1992

Attest:

DOUGLAS B. COMER

Attesting Officer      Acting Commissioner of Patents and Trademarks